United States Patent [19]
Kulzick et al.

[11] Patent Number: 5,393,856
[45] Date of Patent: Feb. 28, 1995

[54] LIQUID PHASE AND AQUEOUS SOLUTIONS OF POLY(VINYL METHYL ETHER) FROM HIGHLY PURIFIED VINYL METHYL ETHER MONOMER

[75] Inventors: Matthew A. Kulzick, Warrenville; Paul A. Koning, Aurora, both of Ill.

[73] Assignee: Amoco Corporation, Chicago, Ill.

[21] Appl. No.: 105,889

[22] Filed: Aug. 11, 1993

[51] Int. Cl.$^6$ ............... C08F 2/06; C08F 6/08; C08F 116/18

[52] U.S. Cl. ............... 526/332; 526/77; 528/495; 528/499; 528/501

[58] Field of Search ............... 526/77, 332; 528/495, 528/499, 501

[56] References Cited

U.S. PATENT DOCUMENTS

| | | | |
|---|---|---|---|
| 2,799,669 | 7/1957 | Zoss | 260/91.1 |
| 3,022,280 | 2/1962 | Shukys | 260/91.1 |
| 3,047,555 | 7/1962 | Arquette | 260/91.1 |
| 3,157,626 | 11/1964 | Heck | 260/91.1 |
| 3,159,613 | 12/1964 | Vanderberg | 260/91.1 |
| 3,228,923 | 1/1966 | Scott et al. | 260/91.1 |
| 3,332,924 | 7/1967 | Van de Castle et al. | 260/91.1 |
| 3,378,537 | 4/1968 | Schultz | 260/91.1 |
| 3,459,723 | 8/1969 | Schultz | 260/91.1 |
| 3,718,634 | 2/1973 | Schultz | 260/91.1 |
| 5,055,536 | 10/1991 | Dubois | 526/194 |
| 5,147,963 | 9/1992 | Plochocka et al. | 526/332 |

FOREIGN PATENT DOCUMENTS 2062213 12/1970 Germany.
896981 12/1960 United Kingdom.

OTHER PUBLICATIONS

Aoshima, Shachi, Kobayashi and Higashimura, "Living Cationic Polymerization of Vinyl Monomers by Organoaluminum Halides, 7. Effect of Basicity and Steric Hindrance of Added Esters on the Living Polymerization of Isobutyl Vinyl Ether with $C_2H_5AlCl_2$." Date of Receipt Sep. 4, 1990.

Kishimoto, Aoshima and Higashimura, "Living Cationic Polymerication of Vinyl Monomers by Organoaluminum Halides. 4. Polymerization of Isobutyl Vinyl Eter by $EtAlCL_2$ in the Presence of Ether Additives". Received Jul. 22, 1988, Revised Manuscript Received Jan. 24, 1989.

*Primary Examiner*—Joseph L. Schofer
*Assistant Examiner*—Tom Weber
*Attorney, Agent, or Firm*—Ronald S. Courtney; Wallace L. Oliver; Mary Jo Kanady

[57] ABSTRACT

A process is disclosed for the preparation of liquid and aqueous solutions of amorphous colorless poly (vinyl methyl ether) polymer with low level of impurities from purified vinyl methyl ether. The polymer has relatively high molecular weight, narrow molecular weight distribution and does not degrade readily due to the presence of impurities. The purification of the monomer uses a procedure selected from the group consisting of a vapor-liquid separation, a solid-liquid separation and combinations thereof to remove the impurities at a temperature within the range of from $-20°$ C. to $+30°$ C. The aqueous solution is prepared by devolitilization of solvent solutions of the polymerized purified vinyl methyl ether monomer. The solid polymer is prepared by heating the aqueous solution of the poly(vinyl methyl ether). The amorphous polymers of poly(vinyl methyl ether) are particularly suited for adhesive applications.

15 Claims, No Drawings

LIQUID PHASE AND AQUEOUS SOLUTIONS OF POLY(VINYL METHYL ETHER) FROM HIGHLY PURIFIED VINYL METHYL ETHER MONOMER

FIELD OF THE INVENTION

This invention relates to liquid phase and aqueous solutions of amorphous poly(vinyl methyl ether) which have a number average molecular weight, $M_n$, above 20,000, a weight average molecular weight, $M_w$, above 80,000, narrow molecular weight distribution comprising a polydispersity of less than 2.5, an intrinsic viscosity within the range of from about 0.4 to 1.0 as measured in chloroform, are water-white and colorless, have low residual impurity levels, and which do not readily degrade due to the presence of impurities. This invention also relates to purification of vinyl methyl ether monomer to remove impurities which can introduce color to the monomer. Also, this invention relates to removal of catalyst residue from poly(vinyl methyl ether) solutions to allow a low catalyst residual to be achieved. The amorphous polymers of vinyl methyl ether are particularly suited for adhesive applications.

DESCRIPTION OF THE PRIOR ART

The purification and polymerization of vinyl alkyl ethers to form amorphous homopolymers is well known. See U.S. Pat. Nos 3,378,537; 3,459,723; 3,718,634 and German Patent No. 2,062,213.

Despite the availability of several commercial and laboratory processes for the production of vinyl alkyl ether homopolymers, there is still a need for improved processes which provide purified, colorless, poly(vinyl methyl ether) containing low levels of trace impurities. Liquid phase amorphous poly(vinyl methyl ether) and its aqueous solutions with low levels of trace impurities, low color, relatively high molecular weight, and narrow molecular weight distribution are useful for the formation of hot-melt and pressure-sensitive adhesives. Amorphous polymers of vinyl methyl ether of too high a molecular weight yield adhesive formulations with inferior surface wetting properties and high viscosities which make them difficult to handle. Amorphous polymers of vinyl methyl ether which contain high levels of residual impurities lack the thermal stability necessary for use in hot-melt adhesives. Amorphous vinyl methyl ether polymers which are not colorless are unsuitable in many adhesive applications particularly in pressure-sensitive adhesives for tapes and labels.

Impure liquid poly(vinyl methyl ether) can be difficult to purify because of physical characteristics including viscosity. Purification of the monomer is accordingly preferable.

Among the many techniques taught in the prior art for purifying vinyl methyl ether monomer, U.S. Pat. Nos. 3,378,537 and 3,459,723 suggest: (1) reacting the monomer over sodium ribbons or a dispersion of sodium at about room temperature to about 50° C.; or (2) water washing the monomer, treating the monomer with potassium hydroxide pellets and then with sodium ribbon or a dispersion as in (1); or (3) refluxing the monomer over sodium ribbon or dispersion under a suitable fractionating column and treating the best fractions with sodium ribbon or dispersion. Other patents suggest the use of active metal hydride reagents such as lithium aluminum hydride or calcium hydride. U.S. Pat. Nos. 3,1 59,613 and 3,157,626 suggests the use of aluminum or titanium alkoxides. All of these methods remove impurities from VME by reacting them with a stoichiometric agent. This is impractical on large commercial scale because these agents are very reactive and therefore difficult to handle, are consumed during the process generating significant amounts of waste, and are quite expensive.

It is generally preferred to remove impurities by an adsorption process. This is very difficult to achieve with vinyl methyl ether due to this monomer's great tendency toward polymerization. In the past, vinyl ether monomers have been purified by adsorption of impurities on alkali metal hydroxides such as potassium hydroxide. This is mentioned in U.S. Pat. Nos. 5,147,963; 3,459,723; 3,047,555; 3,022,280 and 2,799,669. A supported for of alkali metal hydroxide, 10 to 30% metal hydroxide on alumina, is described in German patent No. 2,062,213. Although adsorption of impurities with metal hydroxides or supported metal hydroxides would avoid many of the difficulties encountered with the reactive purification agents described above, we have found that metal hydroxides impart color to vinyl methyl ether monomer and are therefore unsuitable for the preparation of colorless poly(vinyl methyl ether). In U.S. Pat. Nos. 5,055,536 and 3,228,923 molecular sieves are taught to be polymerization catalyst for alkyl vinyl ethers and therefore unsuitable for purification of vinyl methyl ether monomer.

Of the many techniques taught in the prior art for polymerization of vinyl methyl ether to prepare amorphous and crystalline homopolymers having relatively high molecular weights and a narrow molecular weight distribution, a typical procedure relies upon a known Lewis acid initiator in solution of an inert and anhydrous solvent such as an aliphatic or aromatic hydrocarbon such as toluene, a chlorocarbon, or an ether. Typical procedures are taught in U.S. Pat. Nos. 5,147,963; 3,459,723; 3,159,613; 3,047,555; 3,022,280; and 2,799,669. Homopolymers obtained by such processes are described as amorphous, crystalline, and amorphous/crystalline. Weight average molecular weights of the homopolymers are taught as being as low as 10,000 and as high as 300,000 with relatively narrow molecular weight distribution.

Many of the solvents taught in the prior art are quite difficult to remove from poly(vinyl methyl ether) without causing significant degradation of the polymer. Achieving very low levels of these materials is extremely important in many types of adhesive application especially those involving direct skin contact or direct and indirect contact with food.

U.S. Pat. No. 3,332,924 discusses the use of aliphatic hydrocarbon solvents for the polymerization of alkyl vinyl ethers. These solvents particularly the low molecular weight aliphatic hydrocarbons such as butane can be readily removed from poly(vinyl alkyl ether) polymers. Although aliphatic hydrocarbon solvents are suitable for the preparation of most alkyl vinyl ethers, poly(methyl vinyl ether) is not soluble in aliphatic hydrocarbons. It is also well known in the scientific literature that processes catalyzed by Lewis acids occur much more slowly in aliphatic hydrocarbons.

Polymerizations of alkyl vinyl ethers have been conducted in ether solvents. We found however that most ether solvents are too basic and cause the rate of polymerization to be drastically reduced.

The polymerization of vinyl methyl ether has in a few instances been conducted in the absence of solvent, i.e., in pure monomer. This is discussed in U.S. Pat. No. 5,147,963 and German Patent 2,062,213. U.S. Pat. No. 5,147,963 teaches homopolymerization of vinyl methyl ether under the pressure of an added inert gas of about 20 to 100 psi such that the methyl vinyl ether vapor is absorbed into the liquid phase during the polymerization in the substantial absence of a solvent for the methyl vinyl ether vapor. The procedure in U.S. Pat. No. 5,147,963 ignores the problems of heat removal and reaction control which can be substantial upon a commercial level of production. In the German patent, a very specialized piece of machinery was required to perform this bulk polymerization. We have confirmed that the reaction can be carried out in pure monomer but have found that the rate of reaction is extremely rapid which causes significant problems in controlling the reaction and running the reaction safely on a large scale. We have found that a high initial rate of reaction often leads to significant temperature fluctuations during the polymerization. These tend to cause production of discolored polymer and lower the polymer yield.

Numerous Lewis acid catalysts have been described for the polymerization of vinyl alkyl ethers. Many of these result in polymers of inadequate molecular weight or in colored materials. Others require operation at very low temperature which is difficult and expensive to achieve in large commercial equipment. In particular, $BF_3$ gas or a $BF_3$ complex such as an etherate is typically used. However, it has been found that use of $BF_3$ catalyst in the process of the instant invention results in an unacceptable product of an unacceptable color, predominantly yellow, instead of a water-white colorless material. In general, we have found that use of catalysts with high Lewis acidity such as $BF_3$ or $AlCl_3$ tend to produce yellow polymers.

U.S. Pat. No. 3,718,634 teaches a homo or copolymerization process for vinyl methyl ether using an organic aluminum halide in the presence of a cocatalytic amount of water. This catalyst operates at a moderate temperature, $-20$ to $+20°$ C. The catalyst, a dialkyl aluminum halide, is exemplified by diethyl aluminum chloride/water, $DEAC/H_2O$, in a mole ratio of 1/1 to 10/1 in polymerization of vinyl methyl ether in the presence of toluene as solvent. Example IV indicates that a $DEAC/H_2O$ ratio of 5/1, a vinyl methyl ether/toluene ratio of 1 gm/1 cc, and a 0.50 mole % DEAC based on the monomer gave a product with a 0.67 viscosity at 0.1% in benzene. Example V indicates a similar procedure with 0.070 mole % DEAC based on the monomer and results in a viscosity number of 1.30. Example VI, in a similar procedure but with a $DEAC/H_2O$ mole ratio of 10:1, a monomer:toluene ratio of 1:1, and a 0.50 mole % DEAC based on the monomer results in a viscosity number of 2.1, at 0.1% benzene.

Removal of catalyst impurities from poly(vinyl methyl ether) is extremely critical to producing a product with characteristics suitable for use in adhesive formulation. In particular, hot-melt adhesives must have adequate thermal stability to be held at high temperatures for extended periods without suffering degradation. We have found that adequate catalyst removal is critical for achieving this stability with poly(vinyl methyl ether).

U.S. Pat. No. 3,718,634 teaches removing residual alkyl aluminum halide catalyst from amorphous poly(vinyl methyl ether) reaction solutions by quenching with an excess of a lower alcohol or methanolic ammonia or amines and removing catalyst residues by procedures including washing with water and/or methanol. A similar procedure was followed by Nakano et al. in British Patent 896,981. Kishimoto et al. Macromolecules (1989), 22, 3877, and Aoshima et al. Makromol. Chem. (1991), 192, 1749 used a related approach except they added the additional steps of washing the quenched polymer solution with dilute acid and then neutralizing with base.

We have found that these procedures produce a poly(vinyl methyl ether) inferior quality and are not suitable for large scale production. In particular, quenching the reaction mixture with an excess of alcohol followed by washing with water forms finely divided aluminum particles which are not readily separated from the poly(vinyl methyl ether) reaction solution. These particles impart haze to the resultant poly(vinyl methyl ether) product rendering it unsuitable for use in many applications. This problem can be remedied by following the initial wash process with an acid wash as suggested by Aoshima and Kishimoto but residual vinyl methyl ether is rapidly hydrolyzed by acidic water. This renders the recovery and recycle of residual vinyl methyl ether far more difficult. We have further found that washing poly(vinyl methyl ether) reaction solutions with water is often adversely complicated by emulsion formation. If formed, these emulsions greatly hinder the rate of phase separation between the wash water and the poly(vinyl methyl ether) reaction mixtures. Rapid phase separation is critical to achieving efficient, cost effective catalyst removal.

Accordingly, an object of this invention is to provide a vinyl methyl ether polymerization product in the form of either a liquid material or as a viscous, concentrated aqueous solution of amorphous polymeric vinyl methyl ether wherein the polymer has a number average molecular weight, $M_n$, of above 20,000, preferably up to about 120,000, weight average molecular weight, $M_w$, above 80,000, preferably up to about 200,000, with a molecular weight distribution, $M_w/M_n$ of less than 2.5 and the polymer is colorless, water-white, and the I.V. is in the range of from about 0.4 to 1.0 as measured in chloroform using an Ubbelohde viscometer.

Another object of this invention is to provide an improved process for preparation of purified vinyl methyl ether containing low levels of trace impurities to prepare amorphous polymers of vinyl methyl ether which have relatively high molecular weight and narrow molecular weight distribution which amorphous polymers are eminently suitable for pressure-sensitive adhesives and hot-melt adhesives.

Another object of this invention is to provide a purification process for purifying vinyl methyl ether which is carried out without the necessity of using objectionable alkali metal or alkaline earth compounds. Still another object is to provide a purification process which is carried out in the vicinity of room temperature.

SUMMARY OF THE INVENTION

This invention relates to liquid phase and aqueous solutions of poly(vinyl methyl ether) from purified vinyl methyl ether monomer containing low levels of trace impurities. The colorless amorphous polymers of vinyl methyl ether have relatively high molecular weight, narrow molecular weight distribution, an I.V. of 0.4 to 1.0, in the form of a liquid or as a viscous, concentrated aqueous solution of the polymer. The purification of the monomer uses a purification procedure which is carried out in the vicinity of room temperature.

DETAILED DESCRIPTION OF THE INVENTION

In accordance with the present invention, poly(vinyl methyl ether) (PVME) is prepared from vinyl methyl ether monomer which has been purified to obtain a monomer containing low levels of trace impurities, preferably below 750 parts per million. The purification process removes the impurities at a temperature within the range of from −20° C. to +30° C. At temperatures above +30° C., polymerization of the monomer occurs, causing degradation of the monomer, discoloration and loss of yield. Purification of the monomer enables the preparation of a colorless polymer which does not degrade readily due to the presence of impurities and which has a high molecular weight. The purified polymer may crystalize slightly upon standing for prolonged periods. The viscosity of the neat polymer and ready precipitation of polymer from aqueous solution under heat limit distillation purification procedures of the polymer. The purification process of the monomer can use a vapor/liquid extraction procedure with a suitable liquid extractant such as ethylene glycol, or an adsorption procedure using either or both of two types of solid adsorbents: a) nonacidic/basic aluminas or b) base-treated molecular sieves with pore size of up to 10 Angstroms (Å), or a combination of the vapor/liquid extraction procedure and the adsorption procedure using solid adsorbents.

Ethylene glycol in a vapor/liquid extraction can be used to extract impurities comprising water, methanol, ethanol, 1,1-dimethoxyethane and acetaldehyde from vinyl methyl ether. Ethylene glycol is also used effectively to extract these impurities from the monomer by contacting ethylene glycol liquid with the monomer as a vapor in a counter-current extraction. This has the advantage of not requiring a separate distillation step to limit losses in the ethylene glycol.

Other liquids similar to ethylene glycol can be used such as oligomers of ethylene glycol as triethylene glycol and other liquids such as diethylene glycol, diethylene glycol ethyl ether acetate, 2-butoxyethanol, butoxytriglycol, 2-(2-ethoxyethoxy)ethanol, and others.

Solid adsorbents in a purification adsorption procedure other than nonacidic/basic aluminas or small pore molecular sieves treated as in the process of this invention can cause polymerization. For a successful purification procedure, these adsorbents must be used under closely controlled conditions. After thermal activation, the adsorbent must be treated with an inert solvent, either a hydrocarbon or an aromatic such as hexane or toluene, and allowed to cool. Vinyl methyl ether is then allowed to contact the adsorbent at temperatures of from −20° C. to +30° C. At temperatures above −30° C., polymerization occurs causing discoloration and degradation of the monomer. The purification can be viewed typically as a fixed bed process where the monomer is passed through a packed bed of adsorbent.

Prior to thermal activation of the adsorbent, the small pore molecular sieve adsorbent is pretreated with base to prevent polymerization of the vinyl methyl ether. The base is a strong base, the particles of which preferably are too large to fit into the pores of the solid adsorbent, however, the particles of the impurities can enter the pores of the sieve.

Crude vinyl methyl ether monomer typically contains a number of impurities which are detrimental to polymerization of the monomer. It is essential for the process of this invention that these detrimental impurities be removed or at least reduced in concentration to a low level. The impurities present are typically methyl ethyl ether, dimethyl ether, 1,1-dimethoxyethane, ethyl vinyl ether, acetaldehyde, methanol, ethylene glycol and water. Typical level of impurities in crude monomer is shown in Table I.

TABLE 1

| Typical Vinyl Methyl Ether Impurities in Crude Monomer | | |
|---|---|---|
| | Abbreviation | Typical Content (ppm) |
| Methylethyl ether | MEE | 3200 |
| Dimethyl ether | DME | 2500 |
| 1,1-Dimethoxyethane | DMOE | 60 |
| Ethyl vinyl ether | EVE | 500–3000 |
| Acetaldehyde | ACET | 250 |
| Methanol | MeOH | 60 |
| Ethylene glycol | EG | 100 |
| Water | $H_2O$ | 1000 |

By the process of the instant invention, the impurities removed are 1,1-dimethoxyethane, acetaldehyde, methanol, ethylene glycol and water.

In general, the homo or copolymerization process involves adding a catalytic amount of the diethyl aluminum chloride followed by a co-catalytic amount of water to a substantially anhydrous vinyl methyl ether monomer in a non-aromatic, non-chlorinated hydrocarbon solvent of from 2 to 20 carbon atoms. A typical solvent comprises butane. Aromatic solvents and chlorinated solvents are undesirable in food and skin contact applications.

A solvent such as butane is used to control the exotherm reaction of vinyl methyl ether polymerization. The heat of reaction is removed by boiling liquid butane added to the reaction mixture and subsequently condensing the vapor in an external condenser. By selection of the amount of butane added to the reaction, and by control of the pressure and initial temperature of the reaction, the temperature of the polymerization reaction is controlled.

Inadequate temperature control of vinyl methyl ether polymerization has been found to result in loss of control of molecular weight and molecular weight distribution as well as thermal decomposition of the product. The use of butane as a refluxing medium to remove excess heat from the system permits heat control of the refluxing system. Since poly(vinyl methyl ether) is insoluble in butane, the refluxing of butane from the system serves only to remove heat from the system.

Catalyst residues from polymerization of vinyl methyl ether monomer promote degradation of the polymer if not removed after polymerization and result in product of lower molecular weight, yellow color and strong odor. Crude reaction mixtures containing 10 to 50% poly(vinyl methyl ether) are treated with a secondary alcohol such as isopropanol in the presence of a stoichiometric amount of base. This solution is added to water, pH 5 to 9, at 50° to 90° C. to cause precipitation of catalyst residue from the polymer solution. Particle size of catalyst residue is sufficient to allow the catalyst residue to settle to the bottom of the reactor. The residue is removed with the wash water.

In more detail, removal of catalyst residue by use of a secondary alcohol can be by a procedure wherein said poly(vinyl methyl ether) reaction mixture is first contacted with a mixture of a secondary alcohol, selected from the group of secondary alcohols of from 3 to 20 carbon atoms and an alkali metal or alkaline earth hydroxide, where the ratio of the hydroxide to halide in the catalyst is from 0.9 to 1.1 on a molar basis, and where the mixture is subsequently added to water of a pH of 6.5 to 7.5 at a temperature of from 40° C. to 80° C. with agitation for 0.5 to 2 hours, settled for 0.5 to 2 hours and the water and catalyst removed by decantation followed by repeated washing at the above temperature until the wash water is in the range of 6.5 to 7.5.

Alternatively, catalyst residues can be removed from polymerization mixtures wherein said poly(vinyl methyl ether) reaction mixture is first contacted with water containing alkali metal or alkaline earth hydroxides where the ratio of the hydroxide to catalyst is from 4:1 to 10:1 on a molar basis and where the water mixture is maintained at 35° C. to 80° C. This mixture is then agitated for 0.5 to 2.0 hours, settled for 0.5 to 2.0 hours and the water and catalyst removed by decantation followed by repeated water washing until the wash water is in the pH range of 8.0 to 6.0.

Viscous, concentrated aqueous solutions of amorphous polymeric vinyl methyl ether are advantageous since pure poly(vinyl methyl ether) can be highly viscous and difficult to handle. Preferred compositions are aqueous compositions since aqueous solutions can be readily formulated into water dispersible compositions such as water-dispersible adhesives. Solid poly(vinyl methyl ether) can be chopped and homogenized under vacuum by vigorous agitation and addition of water with cooling. Alternatively, solid poly(vinyl methyl ether ) is solubilized in a suitable solvent such as diethylether, methyl t-butylether or vinyl methyl ether. The solvent/poly(vinyl methyl ether) composition is added to water under vacuum at 10° to 30° C. with mixing. After the bulk of the solvent has been removed by application of the vacuum, the vacuum is increased or an inert gas is purged through the system to reduce the residual solvent levels.

The presence of trace impurities in vinyl methyl ether can have a large effect on polymerization. Methanol, acetaldehyde, water and ethylene glycol are potential catalyst poisons and Chain transfer agents. Small amounts of these compounds are typically in crude vinyl methyl ether and prevent polymerization or reduce polymer molecular weight if not efficiently removed.

As noted above, previous investigators have purified impure vinyl methyl ether monomer by passing the monomer through a caustic. Potassium hydroxide removes impurities but can discolor the monomer. It is known that alumina and molecular sieves can remove impurities but, being acidic, can cause polymerization of the monomer.

Surprisingly and unexpectedly, it has been found that basic aluminas and certain size molecular sieves of pore size up to 10 Angstroms (Å) can be used to purify vinyl methyl ether (VME) if proper care is taken. The adsorbent is first activated by heating to activation temperature, typically 200° to 250° C. The adsorbent bed is allowed to cool under a steady flow of nitrogen. When the bed is cooled, a passivation agent is added to the dry bed such as an inert hydrocarbon solvent. There is typically a small exotherm when a dry adsorbent is contacted with a liquid. If vinyl methyl ether (VME) is present at this stage, polymerization will occur, fouling the adsorbent. After the liquid full bed has again cooled to room temperature, VME liquid is added at low temperature −20° C. to +30° C. By keeping the VME cool, polymerization is avoided. This results in a water-white monomer of high purity. Materials such as methanol, water, and acetaldehyde are removed. After the bed has become saturated with impurities, it is regenerated by standard techniques with due care taken to ensure that the bed temperature is not raised until all of the vinyl methyl ether has been removed.

Polymerization techniques of vinyl methyl ether are well-known. However, poly(vinyl methyl ethers) are known to be subject to oxygen, heat and to suffer depolymerization or breakdown in molecular weight to lower molecular weight polymers and to the alcohols from which the monomers are derived. The alcohols can further oxidize to aldehydes, ketones and acids, through the influence of oxygen, heat and light. These influences can cause chain cleavage, cross-linking and reactions with oxygen. Such reactions can be exacerbated by the presence of catalyst impurities from the polymerization reaction.

Removal of polymerization catalyst residue therefore is essential for preparation of poly(vinyl methyl ether) which does not degrade readily due to the presence of impurities. It has been found that a catalyst comprising a alkylaluminum halide can be removed quantitatively by precipitation of the catalyst residue in a water wash in a conventional procedure. Additionally, the use of a water wash procedure to remove catalyst residue is complementary to the preparation of aqueous solutions of poly(vinyl methyl ether) (PVME).

Because of the ease of handling aqueous solutions of PVME as contrasted with the problems of preparing solid block 100% PVME polymer for specific applications, aqueous solutions of PVME are typically preferred such as in applications as water dispersible adhesives. But PVME is insoluble in hot water and at temperatures over 30° C. to 40° C., PVME will begin to precipitate from water in a sudden and near quantitative phase transition. PVME is typically more soluble in many organic solvents than in water and the presence of a small percentage of an organic solvent in PVME can render PVME completely water insoluble. If the solvent is not somewhat water soluble, it will become trapped in the PVME. As the solvent content drops, the solvent vapor pressure goes down. If the vapor pressure of the solvent in the PVME is much below the vapor pressure of water, it will not readily vaporize from the PVME. The rate of solvent evolution is determined by the rate of diffusion of the solvent from the PVME to the water. If the solvent is very insoluble in water, the rate of diffusion from the PVME/solvent phase to the aqueous phase will be very slow. If the solvent is not very volatile, a PVME/solvent sludge will form which is very viscous and cannot be processed with conventional mixing and pumping equipment.

The preparation of aqueous solutions of PVME has been found to be accomplished by solubilizing the polymer in a suitable solvent, most preferably the same solvent system as used in the polymerization, followed by mixing with water and removal of the solvent. The bulk of the solvent is most conveniently removed at moderate pressure conditions, from moderate vacuum to moderate gauge pressure, depending on the boiling point range and solvent characteristics of the solvent system employed. A preferred pressure range for this step is about 500 to 1500 mm Hg (absolute), with the temperature maintained between 0° C. and 40° C., and more preferably between 15° C. and 35° C. After the bulk of the solvent is removed, a stronger vacuum is employed to remove the remaining residual solvent and form the devolatilized aqueous polymer solution. Final vacuum in the range 25 mm Hg to 100 mm Hg, with the temperature held at 25° C. to about 35° C., is generally sufficient for complete removal of the volatile organic solvent.

Water soluble solvents also cannot be used because, first, cationic polymerizations will not occur in polar, water-soluble solvents and second, the affinity of water for water-soluble solvents makes it very difficult to reach a low residual level. Vapor-liquid phase diagrams for water and water soluble solvents such as acetone or methanol typically indicate large amounts of water in the vapor phase as the residual levels drop. Solvents or solvent systems with only partial water solubility, 0.5–10% are preferred, 4–6% being most preferred, with low boiling points, below 150° C. preferred and below 80° C. most preferred, and the ability to dissolve PVME is required. Efficient aqueous solution formations using vinyl methyl ether, diethyl ether, and methyl t-butyl ether have been demonstrated.

In summary, this invention relates to a process for preparation of liquid phase and aqueous solutions of poly(vinyl methyl ether) polymer from purified vinyl methyl ether monomer containing less than 750 parts per million total of impurities comprising water, methanol, ethanol, acetaldehyde, 1,1-dimethoxyethane, and ethylene glycol, said polymer containing less than 100 parts per million total of said impurities in the absence of water and less than 250 parts per million of a non-aromatic, non-chlorinated hydrocarbon solvent of from 2 to 20 carbon atoms, wherein said polymer is water-white colorless, has a number average molecular weight $M_n$ above 20,000, a weight average molecular weight $M_w$ above 80,000, a molecular weight distribution $M_w/M_n$ of less than 2.5, wherein said process comprises:

a) purifying impure vinyl methyl ether monomer containing impurities comprising water, methanol, ethanol, acetaldehyde, 1,1-dimethoxyethane and ethylene glycol to levels less than 750 parts per million (ppm) by extracting said impurities from said monomer by a separation technique selected from the group consisting of a vaporliquid separation, a solid-liquid separation, and combinations thereof, said separation technique characterized as being at a temperature within the range of from about −20° C. to about +50° C. and the said extracted monomer characterized as being water white in color;

b) polymerizing said purified monomer in the presence of an alkyl aluminum halide catalyst and a co-catalyst activator to poly(vinyl methyl ether) polymer in a reaction mixture comprising said monomer and a non-aromatic, non-chlorinated hydrocarbon solvent of from 2 to 20 carbon atoms at a temperature within the range of from about −10° C. to about +20° C. at a pressure sufficient to maintain the reaction mixture in predominantly a liquid state, to prepare poly(vinyl methyl ether) polymer in said reaction mixture;

c) extracting said catalyst and said co-catalyst from said poly(vinyl methyl ether) in said reaction mixture by adding to said reaction mixture a stoichiometric amount of base in water, and, alternatively, in a secondary alcohol selected from the group of secondary alcohols consisting of secondary alcohols of from 3 to 20 carbon atoms and adding the resultant reaction mixture into excess water present as a water wash, at a temperature of from about 0° C. to about 90° C. and a pH of not less than 5 in the aqueous phase wherein said temperature and pH is maintained to cause the said catalyst and said co-catalyst to partition into said wash water, and to remove said catalyst and said co-catalyst from said reaction mixture with said wash water in the absence of hydrolysis and polymerization of unreacted vinyl methyl ether and formation of emulsions to prepare a solvent/poly(vinyl methyl ether) mixture;

d) preparing an aqueous poly(vinyl methyl ether) solution by contacting said solvent/poly(vinyl methyl ether) mixture with a solvent selected from the group of water and water/organic ether ether mixtures at a temperature within the range from about 0° C. to about 35° C. under a vacuum within the range from about 0.1 mm Hg to about 600 mm Hg to remove the solvent by vacuum stripping said solvent and to form a soluble mixture of water and poly(vinyl methyl ether) wherein said aqueous poly(vinyl methyl ether) solution has a poly(vinyl methyl ether) concentration in the range of from 5 to about 70 wt. %, a residual solvent level of less than 250 ppm and total concentration of impurities comprising methanol, ethanol, acetaldehyde, 1,1-dimethoxyethane and ethylene glycol is less than 100 ppm; and e) preparing a solid poly(vinyl methyl ether) polymer by heating said aqueous poly(vinyl methyl ether) solution to a temperature within the range of from about 40° C. to about 100° C. to precipitate said poly(vinyl methyl ether) as a solid from said solution, separating said solid from said solution by solid/liquid separation technique to recover said solid poly(vinyl methyl ether), and heating said solid poly(vinyl methyl ether) under vacuum from about 0.1 mm Hg to about 600 mm Hg to a temperature of from about 100° C. to about 200° C. to remove residual water and solvent from said solid poly(vinyl methyl ether).

In further summary, this invention relates to a process wherein said vapor/liquid separation uses an extractant selected from the group consisting of ethylene glycol, diethylene glycol, diethylene glycol ethyl ether acetate, 2-butoxyethanol, butoxytriglycol, 2-(2-ethoxyethoxy)ethanol, and others; said solid-liquid separation comprising contacting said impurities with a solid adsorbent selected from the group consisting of a nonacid/basic alumina and a small pore molecular sieve of pore size up to 10 Angstroms; wherein said nonacidic/basic alumina has a surface pH greater than 7; and wherein said small pore molecular sieve is selected from the group consisting of number 3A, 4A and 5A molecular sieves which sieve has been treated with a strong base to modify the acidic character of the molecular sieve surface to a pH greater than 7. The said catalyst can comprise diethylaluminum chloride and said co-catalyst can comprise water. The water solubility of said organic ether is within the range of from about 0.5 to about 7 grams per 100 grams of water at 25° C. The said organic ether can be selected from the group consisting of dimethylether, methylethylether, methyl t-butyl ether, vinyl methyl ether, and diethylether.

Additionally, this invention relates to liquid phases and aqueous solutions of poly(vinyl methyl ether) polymer containing less than 100 parts per million of impurities comprising methanol, ethanol, acetaldehyde, 1,1dimethoxyethane, and ethylene glycol, wherein said polymer contains less than 250 parts per million of non-aromatic, non-chloronated hydrocarbon solvent of from 2 to 20 carbon atoms, is water-white, colorless, has a number average molecular weight $M_n$ above 20,000 a weight average molecular weight $M_w$ above 80,000, and a molecular weight distribution $M_w/M_n$ of less than 2.5.

The following examples illustrate the process of this invention but are not to be construed as limiting the scope of the invention.

Example 1

The following illustrates the purification of vinyl methyl ether monomer containing impurities of water, methanol and acetaldehyde, (ACH), 1,1dimethoxyethane, (DMOE) by vapor/liquid extraction and distillation using ethylene glycol as an extractant to scrub the impurities from the monomer.

The columns used had 25–35 trays and were standard 2-inch diameter Oldershaw glass sieve tray columns with vacuum jackets for insulation. Reboiler duties were small, while condenser duty was provided sufficient for total condensation of the purified VME vapor.. Bottoms heat input was provided by circulating about 0.1 GPM of bottoms through an external coil immersed in a water bath. The heat input to the water bath was adjusted to give the desired bottoms temperature. In general, water bath temperatures were 2°–4° C. above the bottoms temperature. The low boiling point required very low coolant temperatures for efficient condensation. This was provided by using Dow Corning 220 Silicone Fluid (2.0 cSt grade) as the coolant, and circulating it through an external dry ice bath to maintain its temperature. Coolant supply temperature was typically about −50° C. There was no detectable VME that failed to condense. The temperature of the ethylene glycol feed to the column was adjusted in the range 15°–30° C. by passing through a small heat exchanger, which was provided with jacket service by a recirculated heating/cooling water bath.

The VME was fed to the column by nitrogen pressure from a cylinder of liquid VME. The VME was vaporized in a coil (⅜-inch tubing, 9 feet long) immersed in a water bath at about 45° C. This gave 100% vaporization of the VME, and delivered the VME vapor to the column at 25°–28° C. (i.e. slightly superheated).

The ethylene glycol feed to the column was heated by a 2-sq. ft. Young heat exchanger serviced with water from a water bath. The heat exchanger was oversized, so that there was negligible temperature difference required. Conditions and results are in Table 2.

TABLE 2

| Run | A | B | C |
|---|---|---|---|
| No. of Trays | 25 | 25 | 35 |
| EG Feed Tray | 3 | 3 | 3 |
| VME Feed Trays | 21 | 25 | 35 |
| Reflux Ratio | 0.3 | 0 | 0 |
| VME Feed Rate (g/hr) | 1693 | 1997 | 1907 |
| EG Feed Rate (g/hr) | 1970 | 2982 | 4017 |
| VME Feed Composition (ppm) | | | |
| ACH | 3368 | 3500 | 1425 |
| Methanol | 2282 | 2400 | 0 |
| DMOE | 784 | 1000 | 0 |
| Water | 1527 | 1950 | 2225 |
| Distillate Composition (ppm) | | | |
| ACH | 780 | 483 | 198 |
| DMOE | 307 | 300 | 0 |

TABLE 2-continued

| Run | A | B | C |
|---|---|---|---|
| Tray 23 Temperature (°C.) | 18 | 25.8 | 24.5 |

Note: Tray numbering starts from the top tray as Tray 1.

Example 2

The following illustrates the purification of vinyl methyl ether monomer containing impurities of water, methanol, dimethoxyethane, and acetaldehyde by adsorption using nonacidic alumina to remove the impurities from the monomer.

The alumina adsorbent was activated by heating to 200° C. to 250° C. under nitrogen. The adsorbent is then allowed to cool to room temperature. The bed is then wetted with an inert solvent selected from the group consisting of aliphatic hydrocarbons such as butane, pentane or hexane and aromatic hydrocarbons such as toluene and xylene and allowed to cool to room temperature. The solvent is then drained from the bed and liquid VME introduced. By wetting the bed prior to introduction of VME, exotherms are avoided which initiate VME polymerization. The crude VME is then allowed to flow through the bed at a flow rate of 1 to 4 liters VME per liter adsorbent per hour. The purified VME was collected and the purify of this product monitored by conventional techniques such as gas chromotography. When impurities are detected appearing in the purified monomer, the VME flow rate is stopped, the adsorption beds drained back into the crude VME feed and blown dry under nitrogen but not heated. The bed is then rinsed with a polar organic solvent such as acetone, methanol, or ethanol. After rinsing from 10 minutes to 2 hours, the polar organic solvent is drained and the bed regenerated by heating to 200° C. to 250° C. under nitrogen. The purification process can then be repeated.

The procedure of this example used an adsorption bed filled with approximately 2000 g of Selexsorb COS alumina from Aluminum Company of America (Alcoa) in the form of 3/16 inch spheres. The bed was heated to 200° C. to 250° C. for over eight hours under a small, 3 to 5 scfm, flow of nitrogen. The bed was then allowed to cool under nitrogen. The beds were then filled with hexane which generated a 10° C. to 15° C. exotherm, allowed to cool, and drained. Liquid VME was then added and allowed to flow through the bed at a rate of from 2500 to 4000 g per hour until impurities especially methanol began appearing in the purified VME product. The beds were then drained and dried with nitrogen, rinsed with acetone for 2 to 4 hours and regenerated by heating to 200° C. for over 8 hours under a nitrogen flow of 3 to 5 scfm (standard cubic feet per minute). The bed could then be reused for purification.

This yielded a purified vinyl methyl ether with a methanol, ethylene glycol, ethanol, acetaldehyde, and water concentration below 50 ppm and with a Gardner color of less than 1.

Example 3

The procedure of Example 2 was repeated with molecular sieves, 3A and 4A molecular sieves, which have pore sizes of from 3 Angstrom (Å) units and 4 Angstrom (Å) units, wherein the adsorbent molecular sieves were pretreated with a base to prevent polymerization. These small pores readily adsorb small molecules such as methanol and water. The 3A and 4A molecular sieves are treated with a large molecule which is a strong base but which is too large to fit into the sieve pores. The surface of the sieve, which is acidic, is therefore modified to be non-acidic but the interior of the sieve pores retains the acidic character of the sieve and therefore the aggressive adsorption characteristics of a standard acidic sieve. Suitable bases include $R_3N$ where R is an aliphatic or aromatic hydrocarbon or hydrogen. The three R groups are the same or different. Examples are butyl amine, tributylamine, or methylethylamine. The base can be an aromatic amine such as pyridine, or any of the many related compounds. The base can be an alkoxide such as potassium t-butoxide or a hydroxide. Any strong base which would react with a molecular sieve to modify the amount of acidity of the molecular sieves surface to a pH greater than 7 is suitable.

The procedure of this example used 3A and 5A sieves obtained from Davison Chemical Division. These were activated by heating to 120° C. in a vacuum oven overnight and cooling under nitrogen. They were reacted with a 5% solution of pyridine in pentane by swirling the sieve in the solution for one hour. The sieves were isolated by decanting off the pyridine solution and then rinsing with pentane three times. The sieves were dried in vacuo with no heating.

Vinyl methyl ether (VME) was exposed to the sieve by placing 1 g of sieve in a miniert vial and then adding 10 g of monomer and allowing to equilibrate for several hours or overnight. The composition of the VME was determined by standard procedures.

Results are shown in Table 3. In general, the untreated molecular sieves cause formation of both DMOE and poly(vinyl methyl ether). Both of these products are formed by acid catalyzed mechanisms. In both cases, treating the sieve with base significantly reduces the formation of the above species. This treatment however does not interfere with the ability of the sieve to remove impurities such as methanol and acetaldehyde. The 3A sieve fails to remove acetaldehyde since this species is too large to fit in its small three angstrom pores. Details are in Table 3.

TABLE 3

Effect Of Added Pyridine To The Adsorption

| Sample | Acetaldehyde (PPM) | DMOE (PPM) | MeOH (PPM) | % Polymer |
|---|---|---|---|---|
| Crude VME | 1,930 | 741 | 2,000 | 0.57 |
| Davison 3A Untreated | 1,875 | 979 | 86 | .61 |
| Davison 5A Untreated | 719 | 2,451 | 90 | 35 |
| Davison 3A Treated | 1,817 | 809 | 48 | 0.42 |
| Davison 5A Treated | 443 | 854 | nd | 0.50 |

Example 4

The following illustrates the polymerization of vinyl methyl ether. Vinyl methyl ether is polymerized in butane using a diethyl aluminum chloride/water catalyst. The reaction is allowed to proceed for 3-6 hours and then quenched using a conventional laboratory technique. The polymer is isolated, dried in vacuo, and analyzed by both inherent viscosity and gel permeation chromatography.

A two gallon stainless steel reaction (PARR model 4552) was used for the polymerization. The reaction is equipped with: an overhead condenser, external cooling jacket, internal cooling coils, a 4-blade pitched turbine agitator, bottom drain valve, VME addition port, catalyst addition port, nitrogen/vacuum port, thermocouple and emergency relief line. The overhead condenser, external and internal cooling coils are chilled with a silicone fluid using a Haake circulating chiller.

C. P. grade n-butane was obtained from Matheson Gas Products and was used without further purification. VME was purified as described in Example 1. Diethyl aluminum chloride was 15 wt. % in hexane and was used as received. Water was purified through an cartridge type deionization system.

The reactor is evacuated then filled with dry nitrogen. This cycle is repeated three times. Water, 0.154 grams, is added to a sample addition loop on the VME feed line to the reactor. This water is then carried into the reactor by the addition of 1417.7 grams of VME through the sample addition line. Butane, 607.3 grams, is then added to the reactor. The agitator is then set to 120 rpm and the reactor is cooled to 10° centigrade using the cooling coils. The 15 wt % solution of DEAC, 34.42 grams, is then charged to a 150 ml Hoke vessel, pressurized to 25 psig with dry nitrogen and added to the reactor via the nitrogen pressure. The exotherm of reaction is noticed almost immediately. This heat of reaction is balanced by the circulation of chilled silicon fluid to the coils and heat exchanger so a near constant temperature of 10° centigrade is maintained. The reaction was allowed to run for 5 hours. The reaction is then quenched by emptying the reactor contents into a vented 5 liter three neck reactor containing 50 grams sodium sulfate decahydrate and 1000 ml toluene via the bottom drain valve. One side arm of the 3 neck reactor was used for addition of reactor contents, the other for venting unreacted VME and butane. The 3 neck reactor was equipped the a overhead stirrer. The contents are then stirred overnight and allowed to come to room temperature.

The reaction mixture is then filtered through a Buchner funnel. This gives a clear, thick solution of poly(vinyl methyl ether). Most of the toluene is then removed by rotary evaporation and the polymer further dried by heating to 50° to 60° C. in a vacuum oven overnight. This yields a clear, colorless to slightly yellow, tacky viscous liquid. Yield based on monomer charge was 34 wt. % at a reaction temperature of 10° C. PVME polymer can be characterized by inherent viscosity (IV) {0.6 grams/dL solution of product in chloroform}. Typical IV of PVME is IV of 0.6 to 1.0 with an $M_n=30,000-55,000$ g/mole and $M_w=70,000-120,000$ g/mole. The inherent viscosity (IV) of the polymer obtained by the process of this example was 0.6.

Example 5

Vinyl methyl ether polymerized in the presence of a Lewis acid catalyst as in Example 4 can contain catalyst residues which must be removed. A variety of techniques have been utilized form removing alkyl aluminum chloride catalysts from poly(vinyl ether) solutions. As noted earlier, Schultz, U.S. Pat. No. 3,718,634, removed catalyst by first treating with methanol and then washing with water or by treating with methanol/ammonia solutions. A similar procedure was used by Nakano, et al., GB Patent 869,981. Kishimoto, et al., Macromolecules, 1989, 22, 3877-3882. Aoshima, et al. Makromol. Chem., 1991, 192, 1749-1757, used a related approach except additional steps were added of washing the quenched polymer solution with dilute acid and then neutralizing with base.

In the procedure of this example, crude reaction mixtures containing 10-50% poly(alkyl vinyl ether) are first treated with an alcohol of 1 to 20 carbon atoms such as isopropanol in the presence of a stoichiometric amount of base. This solution is then added to water, pH 5-9, at 0° C. to 90° C. This causes precipitation of catalyst residues from the polymer solution. When the process is conducted in this manner, the particle size of the catalyst residues is sufficient to allow the residue to settle to the bottom of the wash reactor. The residues can then be readily removed with the wash water. This results in a fairly rapid, efficient catalyst separation. Polymer resulting from this process is colorless and haze-free.

This example entails a two step procedure. First, a mixture of MOH and ROH are added to the crude poly(alkyl vinyl ether)/solvent reaction mixture. M can be any group IA or IIA metal such as lithium, potassium, sodium, etc. R can be any alkyl group but secondary alkyl groups such as isopropyl, s-butyl, etc. are preferred. This reaction is generally conducted at or near the polymerization temperature, about 0° C. The amount of MOH and ROH depends on the amount and type of alkyl aluminum used as catalyst. The amount of ROH should be from 3 to 100 x the amount of alkyl aluminum on a molar basis. The amount of MOH should be 0.9-1.1 x the amount of chloride in the alkyl aluminum chloride on a molar basis. A MOH/chloride ratio of 0.95-1.05 is preferred. In the second step, this quenched solution is added to water at 50°-70° C. with agitation.

Example 6

The following illustrates an alternative procedure for removing the catalyst from the poly(vinyl methyl ether) reaction mixture. The reaction mixture is added to a solution of a alkali metal hydroxide in water as a wash, where the amount of hydroxide is in the range of 4:1 to 10:1 on a molar basis with respect to catalyst. The water is maintained at a temperature of between 40° C. to 60° C. and is agitated for 0.5 to 2 hours. The mixture is then allowed to settle, phase separate and the aqueous alkali wash layer is removed. The pH of this alkali wash layer after separation is above 12.

The poly(vinyl methyl ether) reaction mixture is then contacted with a water wash where the water is between a pH of 6.5 to 7.5 before addition. This mixture is maintained at a temperature between 40° C. to 60° C. and is agitated for 0.5 to 2 hours. The mixture is then allowed to settle, phase separate and the water wash layer is removed. The pH of this wash layer after separation is above 10.

This process of contacting the poly(vinyl methyl ether) reaction mixture with a water wash at pH 6.5 to 7.5, maintaining at 40° C. to 60° C., agitating, settling and removal of the water wash layer is continued until the separated wash water has a pH of 7.0 to 9.0.

This procedure allows the catalyst to be removed without allowing the pH of the aqueous layer to become acidic and hence avoiding hydrolysis of unreacted vinyl methyl ether. This process additionally allows the removal of the catalyst without the formation of colloidal or emulsified solid alumina species due to the high final pH of the first two washes.

Example 7

The following example illustrates the difficulty of preparing aqueous solutions of poly(vinyl methyl ether) (PVME) from 100% polymer. PVME exists as a highly viscous liquid. Aqueous solutions of the polymer are preferred because of ease of handling and environmental aspects.

Dispersion of solid PVME into a fluid requires size reduction of the solid to particles sized for dissolution in the fluid.

A Ross Versa Mix which has an emulsifier, a high speed disperser, and an anchor (a three-wing agitation) was used to prepare a 30% PVME aqueous solution from solid block PVME.

Ten pounds of block PVME were manually cut into pieces and added to 23 pounds of distilled water in a three-gallon stainless steel beaker equipped with the Ross Versa Mix. The mixture was agitated at 70 rpm anchor speed and 400 rpm disperser speed. The PVME was dissolved after mixing for 12 hours at ambient temperature.

Example 8

The following example illustrates the preparation of aqueous solutions of PVME using a solvent to solubilize PVME wherein the solvent is removed from the solution of PVME by addition of water with concurrent application of high vacuum to devolatilize the solvent/water/PVME solution at a temperature within the range of from about 10° C. to about 30° C. After the bulk of the solvent has been removed, the vacuum is increased or an inert gas is purged through the system to further reduce the residual solvent levels. With appropriate choice of solvent and conditions, an aqueous PVME solution is prepared with low residual solvent level without the necessity of isolating 100% liquid PVME. Preferred solvents were found to be those with boiling points below 150° C. at atmospheric pressure. Solvents with a boiling point below 80° C. with a solubility in water at 25° C. of at least 0.5%, preferably greater than 4%, are preferred, such as diethylether, dimethylether, methylethylether, methyl t-butylether and vinyl methyl ether.

To maintain the PVME in solution, the devolatilization must be at a temperature within the range of between 10° C. and 30° C. at atmospheric pressure as over 30° C. to 35° C., PVME precipitates from water in near quantitative amounts. Accordingly, temperatures above 30° C. cannot be used to drive traces of solvent from the solvent/water/PVME solution.

All runs were conducted in a 2 L reactor fitted with an overhead stirrer, a polymer solution feed pump, a water jacket, and a dry ice condenser fitted with a solvent receiver. Initially approximately 500 ml of water was placed in the reactor and a vacuum placed on the reactor. The system pressure was chosen so the solvent could be removed rapidly and condensed efficiently. A 20-30% solution of PVME in solvent was then added to the reactor over a period of 1-2 hours depending on the rate of solvent removal and the appearance of the reactor contents. A quantity of polymer solution was added to generate approximately a 40% aqueous solution. After all the solution was added and the bulk of the solvent removed, the vacuum was increased to complete the devolatilization process. In some experiments, a nitrogen purge stream was also added to further reduce the volatiles level. Results of these runs are listed in Table 3.

TABLE 4

Residual Solvent and Intermediate Solvent Levels from PVME Devolatilization

| Solvent | Temp. (°C.) | Press. (mbar) | Residual (ppm) | Homogeneity |
|---|---|---|---|---|
| Acetone | 13 | 11.2 | 970 | yes |
| Methanol | 10 | 4 | 64,000 | yes |
| Methylenechloride | 20 | 4 | 1900 | no |
| Toluene | 21 | 4 | 1900 | no |
| Methyl t-butyl-ether[4] | | | | |
| a | 25 | 250 | 370,000 | yes |
| b | 8 | 4 | n.d.[1] | |
| Diethylether[4] | | | | |
| a | 25 | 230 | 140,000 | yes |
| b | 18 | 5 | n.d. | |
| VME | | | | |
| a | 25 | 760 | ~57,000[2] | no |
| b | 20 | 6 | 330[3] | |

[1] n.d.—not detectable, <20 ppm
[2] 1.7% VME, 3.8% dimethoxyethane, 0.2% acetaldehyde
[3] 200 ppm VME, 100 ppm dimethoxyethane, 30 ppm acetaldehyde
[4] a Sample taken after completion of solution addition and bulk solvent removal, about one hour.
b Final sample, about four hours.

Success of a particular solvent has been found to be gauged by two variables, the ultimate residual level and the homogeneity of the reactor contents. When the solvent was very water soluble like methanol and acetone, the reactor contents remained homogeneous, allowing efficient stirring and no operational difficulties but a low residual level could not be reached. Solvents with low solubility in water, such as methylene chloride and toluene, gave fairly low residual levels but the mixture was inhomogeneous. The PVME phase separated during the process forming a highly viscous goo which severely interfered with efficient agitation. With toluene, the agitator froze up at several points.

Of the solvents tested ethers worked the best. Diethylether and methyl t-butyl ether appear to have enough water solubility to prevent PVME from forming a viscous phase but are not so soluble in water than they cannot be removed. It was surprising that methyl t-butyl ether worked better than other more volatile solvents such as acetone and dichloromethane. This is apparently due to water solubility. VME also worked well despite its low water solubility. The VME system did become inhomogeneous in the reactor but the high VME vapor pressure apparently compensated for its low water solubility.

Example 9

The following example illustrates the preparation of a liquid phase PVME polymer. The PVME polymer prepared as an aqueous solution in Example 8 is heated to a temperature greater than about 40° C. to about 100° C. at atmospheric pressure to cause the PVME polymer to phase separate and coalesce as a high-solids, low water product wherein the phase separated water is removable by conventional means. The high solids, low-water polymer is dried under vacuum of from 0.1 mm Hg to about 600 mm Hg to a water content to less than about 2 wt. %.

600 g aqueous PVME from Example 8 is placed in a 1 L round-bottom flask equipped with a heating mantle and thermocouple. The contents are heated to 55° C under nitrogen until the polymer is entirely coalesced and the PVME separates into two phases, water and polymer. The water is decanted. The polymer is dried by use of a rotary evaporator at a temperature of 90° C. and a vacuum of 600 mm Hg, for a period of 120 minutes. The PVME polymer has a water content of less than 0.5 wt. %.

That which is claimed is:

1. A process for preparation of liquid phase and aqueous solutions of poly(vinyl methyl ether) polymer from purified vinyl methyl ether monomer containing less than 750 parts per million total of impurities comprising water, methanol, ethanol, acetaldehyde, 1,1-dimethoxyethane, and ethylene glycol, said polymer containing less than 100 parts per million total of said impurities in the absence of water and less than 250 parts per million of a non-aromatic, non-chlorinated hydrocarbon solvent of from 2 to 20 carbon atoms, wherein said polymer is water-white, colorless, has a number average molecular weight $M_n$ above 20,000, a weight average molecular weight $M_w$ above 80,000, a molecular weight distribution $M_w/M_n$ of less than 2.5, wherein said process comprises:

a) purifying impure vinyl methyl ether monomer containing impurities comprising water, methanol, ethanol, acetaldehyde, 1,1-dimethoxyethane and ethylene glycol to levels less than 750 parts per million (ppm) by extracting said impurities from said monomer by a separation technique selected from the group consisting of a vapor-liquid extraction separation, a solid-liquid adsorption separation, and combinations thereof, said separation technique characterized as being at a temperature within the range of from about −20° C. to about +50° C. to about +50° C. and the said extracted monomer characterized as being water white in color;

b) polymerizing said purified monomer in the presence of an alkyl aluminum halide catalyst and a co-catalyst activator to poly(vinyl methyl ether) polymer in a reaction mixture comprising said monomer and a non-aromatic, non-chlorinated hydrocarbon solvent of from 2 to 20 carbon atoms at a temperature within the range of from about −10° C. to about +20° C. at a pressure sufficient to maintain the reaction mixture in predominantly a liquid state, to prepare poly(vinyl methyl ether) polymer in said reaction mixture;

c) extracting said catalyst and said co-catalyst from said poly(vinyl methyl ether) in said reaction mixture by adding to said reaction mixture a stoichiometric amount of base in water, and, alternatively, in a secondary alcohol selected from the group of secondary alcohols consisting of secondary alcohols of from 3 to 20 carbon atoms and adding the resultant reaction mixture into excess water present as a water wash, at a temperature of from about 0° C. to about 90° C. and a pH of not less than 5 in the aqueous phase wherein said temperature and pH are maintained to cause the said catalyst and said co-catalyst to partition into said wash water, and to remove said catalyst and said co-catalyst from said reaction mixture with said wash water in the absence of hydrolysis and polymerization of unreacted vinyl methyl ether and formation of emulsions to prepare solvent/poly(vinyl methyl ether) mixture;

d) preparing an aqueous poly(vinyl methyl ether) solution by contacting said solvent/poly(vinyl methyl ether) mixture with a solvent selected from the group of water and water/organic ether mixtures at a temperature within the range from about 0° C. to about 35° C. under a vacuum within the range from about 0.1 mm Hg to about 600 mm Hg to remove the solvent by vaccum stripping said solvent to form a soluble mixture of water and poly(vinyl methyl ether) wherein said aqueous poly(vinyl methyl ether) solution has a poly(vinyl methyl ether) concentration in the range of from 5 to about 70 wt. %, residual solvent level of less than 250 ppm and total concentration of impurities comprising methanol, ethanol, acetaldehyde, 1,1-dimethoxyethane and ethylene glycol is less than 100 ppm; and, alternatively, e) preparing a solid poly(vinyl methyl ether) polymer by heating said aqueous poly(vinyl methyl ether) solution to a temperature within the range of from about 40° C. to about 100° C. to precipitate said poly(vinyl methyl ether) as a solid from said solution, separating said solid from said solution by solid/liquid separation technique to recover said solid poly(vinyl methyl ether), and heating said solid poly(vinyl methyl ether) under vacuum from about 0.1 mm Hg to about 600 mm Hg to a temperature of from about 100° C. to about 200° C. to remove residual water and solvent from said solid poly(vinyl methyl ether).

2. The process of claim 1 wherein said purifying impure vinyl methyl ether monomer by vapor-liquid extraction separation uses an extractant selected from the group consisting of ethylene glycol, diethylene glycol, diethylene glycol ethyl ether acetate, 2-butoxyethanol, butoxytriglycol and 2-(2-ethoxyethoxy)ethanol.

3. The process of claim 2 wherein said extraction of said impurities is by vapor-liquid extraction separation of said impurities, using ethylene glycol as an extractant.

4. The process of Claim 1 wherein said purifying impure vinyl methyl ether monomer by said solid-liquid adsorption separation comprises extraction of said impurities by contacting said impurities with a solid adsorbent selected from the group consisting of a nonacid/basic alumina and a small pore molecular sieve of pore size up to 10 Angstroms (Å) which has been treated with a strong base.

5. The process of claim 4 wherein said nonacidic/basic alumina has a surface pH greater than 7.

6. The process of claim 4 wherein said small pore molecular sieve treated with a strong base is selected from the group consisting of number 3A, 4A and 5A molecular sieves which has been treated with a strong base to modify the acidic character of the molecular sieve surface to a pH greater than 7.

7. The process of claim 1 wherein said catalyst comprises diethylaluminum chloride and said co-catalyst comprises water.

8. The process of claim 1 wherein water solubility of said organic ether is within the range of from about 0.5 to about 7 grams per 100 grams of water at 25° C.

9. The process of claim 8 wherein said organic ether is selected from the group consisting of dimethyl ether, methyl ethyl ether, methyl t-butyl ether, vinyl methyl ether, and diethylether.

10. The process of claim 1 wherein said extraction of impurities in said monomer is by contacting said impurities with a solid adsorbent selected from the group consisting of a nonacidic/basic alumina and a small pore molecular sieve treated with a strong base.

11. The process of claim 1 wherein said extraction of impurities in said monomer is by vapor-liquid extraction separation of said impurities using ethylene glycol.

12. The process of claim 1 wherein said levels of impurities in said monomer are reduced by a procedure selected from the group consisting of vapor-liquid separation of said impurities using ethylene glycol, solid-liquid adsorption separation comprising contacting said impurities with a solid adsorbent selected from the group consisting of a nonacidic/basic alumina and a small pore molecular sieve treated with a strong base, and combinations thereof.

13. The process of claim 1 wherein said poly(vinyl methyl ether) reaction mixture is first contacted with a mixture of a secondary alcohol, selected from the group of secondary alcohols consisting of secondary alcohols of from 3 to 20 carbon atoms and an alkali metal or alkaline earth hydroxide, where the ratio of the hydroxide to halide in the catalyst is from 0.9 to 1.1 on a molar basis, and where the mixture is subsequently added to water of a pH of 6.5 to 7.5 at a temperature of from 40° C. to 80° C. with agitation for 0.5 to 2 hours, settled for 0.5 to 2 hours and the water and catalyst removed by decantation followed by repeated washing at the above temperature until the wash is in the range of 6.5 to 7.5.

14. The process of claim 1 wherein said poly(vinyl methyl ether) reaction mixture is first contacted with water containing alkali metal or alkaline earth hydroxides where the ratio of the hydroxide to catalyst is from 4:1 to 10:1 on a molar basis and where the water mixture is maintained at 35° C. to 80° C., wherein said mixture is then agitated for 0.5 to 2.0 hours, settled for 0.5 to 2.0 hours and the water and catalyst removed by decantation followed by repeated water washing until the wash water is in the pH range of 8.0 to 6.0.

15. The poly(vinyl methyl ether) polymer prepared by the process of claim 1.

* * * * *

UNITED STATES PATENT AND TRADEMARK OFFICE
CERTIFICATE OF CORRECTION

PATENT NO. : 5,393,856
DATED : February 28, 1995
INVENTOR(S) : Matthew A. Kulzick, Paul A. Koning It is certified that error appears in the above-indentified patent and that said Letters Patent is hereby corrected as shown below:

| Col. | Line | |
|------|------|---|
| 2 | 15 | "A supported for of alkali metal hydroxide," should read --A supported form of alkali metal hydroxide,-- |
| 12 | 27 | "VME was collected and the purify of this product" should read --VME was collected and the purity of this product-- |

Signed and Sealed this

Eleventh Day of November, 1997

Attest:

BRUCE LEHMAN

Attesting Officer      Commissioner of Patents and Trademarks